(12) United States Patent
Tanaka et al.

(10) Patent No.: US 11,103,179 B2
(45) Date of Patent: Aug. 31, 2021

(54) SWALLOWING SENSOR AND SWALLOWING ABILITY DIAGNOSIS SYSTEM PROVIDED WITH THE SAME

(71) Applicant: Murata Manufacturing Co., Ltd., Kyoto (JP)

(72) Inventors: Kenji Tanaka, Kyoto (JP); Toru Yabe, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 387 days.

(21) Appl. No.: 16/184,391

(22) Filed: Nov. 8, 2018

(65) Prior Publication Data

US 2019/0069833 A1 Mar. 7, 2019

Related U.S. Application Data

(63) Continuation of application No. PCT/JP2017/017158, filed on May 1, 2017.

(30) Foreign Application Priority Data

May 13, 2016 (JP) .............................. JP2016-097304
May 13, 2016 (JP) .............................. JP2016-097307

(51) Int. Cl.
*A61B 5/00* (2006.01)
*A61B 5/11* (2006.01)
(Continued)

(52) U.S. Cl.
CPC .............. *A61B 5/4205* (2013.01); *A61B 5/00* (2013.01); *A61B 5/08* (2013.01); *A61B 5/11* (2013.01);
(Continued)

(58) Field of Classification Search
CPC ....... A61B 5/4205; A61B 5/08; A61B 5/6822; A61B 5/6833; A61B 7/008; A61B 5/4211;
(Continued)

(56) References Cited

U.S. PATENT DOCUMENTS 6,169,915 B1 * 1/2001 Krumbiegel ............. A61B 5/00
600/372
7,236,820 B2 * 6/2007 Mabary .................. A61B 5/037
600/547
(Continued)

FOREIGN PATENT DOCUMENTS

JP 2001-137202 A 5/2001
JP 2005-224439 A 8/2005
(Continued)

OTHER PUBLICATIONS

Machine translation of WO 2015064216 A1 retrieved from worldwide.espacenet.com on Jan. 13, 2021 (Year: 2015).*
(Continued)

*Primary Examiner* — May A Abouelela
(74) *Attorney, Agent, or Firm* — Pearne & Gordon LLP

(57) ABSTRACT

A swallowing sensor that is attached to a person's pharyngeal portion and that measures the person's swallowing ability includes: a film-shaped detector that detects vibration based on displacement and sound of the pharyngeal portion; an adhesive layer that is provided on one of two main sides of the detector and that attaches the detector to the pharyngeal portion; and a sensing film arranged on the detector to cover entirety of the other main side of the detector, wherein a main side of the sensing film that contacts the detector contains an adhesive component, the sensing film is attachable to the pharyngeal portion around the detector using the adhesive component, and the sensing film conveys vibration (Continued)

to the detector. Accordingly, the swallowing ability can be more accurately measured.

11 Claims, 11 Drawing Sheets

(51) Int. Cl.
 *A61B 5/08* (2006.01)
 *A61B 7/00* (2006.01)
(52) U.S. Cl.
 CPC .......... *A61B 5/6822* (2013.01); *A61B 5/6833* (2013.01); *A61B 5/7282* (2013.01); *A61B 7/008* (2013.01); *A61B 2562/0261* (2013.01); *A61B 2562/164* (2013.01)
(58) Field of Classification Search
 CPC ... A61B 5/4216; A61B 5/4222; A61B 5/4233; A61B 5/4238; A61B 5/7282; A61B 2562/0261; A61B 2562/164; G01N 2800/14
 USPC ......................................... 600/301, 431, 593
 See application file for complete search history.

(56) References Cited

U.S. PATENT DOCUMENTS

| | | | |
|---|---|---|---|
| 7,651,470 B2* | 1/2010 | Sato | A61B 5/1128 |
| | | | 600/587 |
| 8,287,470 B2* | 10/2012 | Kandori | A61B 5/6822 |
| | | | 600/586 |
| 10,828,007 B1* | 11/2020 | Telfort | A61B 7/02 |
| 2005/0187348 A1* | 8/2005 | Sonobe | C09J 7/385 |
| | | | 525/154 |
| 2005/0283096 A1* | 12/2005 | Chau | A61B 5/6822 |
| | | | 600/593 |
| 2009/0227907 A1* | 9/2009 | Kandori | A61B 5/11 |
| | | | 600/593 |
| 2010/0056961 A1* | 3/2010 | Voloschin | A61B 5/394 |
| | | | 600/593 |
| 2012/0265103 A1* | 10/2012 | Policker | G16H 15/00 |
| | | | 600/593 |
| 2013/0183660 A1 | 7/2013 | Yu et al. | |
| 2013/0197321 A1* | 8/2013 | Wilson | A61B 5/0826 |
| | | | 600/301 |
| 2013/0310661 A1* | 11/2013 | Jedwab | A61B 5/6822 |
| | | | 600/301 |
| 2015/0112150 A1* | 4/2015 | Bernhard | A61B 5/6822 |
| | | | 600/301 |
| 2016/0026767 A1* | 1/2016 | Sarrafzadeh | A61B 5/6822 |
| | | | 600/586 |
| 2016/0218687 A1 | 7/2016 | Takata | |
| 2016/0256665 A1* | 9/2016 | Doshi | A61M 1/0088 |
| 2016/0372653 A1 | 12/2016 | Umeda et al. | |

FOREIGN PATENT DOCUMENTS

| | | | | |
|---|---|---|---|---|
| JP | 2013-533040 A | 8/2013 | | |
| WO | WO-2010033819 A1 * | 3/2010 | ........... | H01L 41/042 |
| WO | WO-2010102310 A2 * | 9/2010 | ........... | A61B 5/6882 |
| WO | 2015/053241 A1 | 4/2015 | | |
| WO | 2015/064216 A1 | 5/2015 | | |
| WO | WO-2015064216 A1 * | 5/2015 | ........... | G01L 1/16 |
| WO | 2015/133422 A1 | 9/2015 | | |

OTHER PUBLICATIONS

International Search Report for International Application No. PCT/JP2017/017158 dated Aug. 1, 2017.
Written Opinion for International Application No. PCT/JP2017/017158 dated Aug. 1, 2017.

* cited by examiner

SWALLOWING SENSOR AND SWALLOWING ABILITY DIAGNOSIS SYSTEM PROVIDED WITH THE SAME

This is a continuation of International Application No. PCT/JP2017/017158 filed on May 1, 2017 which claims priority from Japanese Patent Application No. 2016-097304 filed on May 13, 2016, and Japanese Patent Application No. 2016-097307 filed on May 13, 2016. The contents of these applications are incorporated herein by reference in their entireties.

BACKGROUND

Technical Field

The present disclosure relates to a swallowing sensor and a swallowing ability diagnosis system provided with the same.

Hitherto, a swallowing sensor that is attached to a person's pharyngeal portion and that measures the person's swallowing ability has been proposed (for example, see Patent Document 1).

The swallowing sensor of Patent Document 1 evaluates, with the use of two piezoelectric elements, the number of times and the strength of a subject's swallowing. Specifically, the first piezoelectric element is an element that changes the amount of electric charge in accordance with the amount of displacement of a bone (thyroid cartilage) in a subject's pharyngeal portion and generates an electric charge signal (displacement signal) in accordance with the change. The second piezoelectric element is an element that changes the amount of electric charge in accordance with the intensity of sound of the pharyngeal portion which is made at the time of swallowing (swallowing sound) and generates an electric charge signal (audio signal) in accordance with the change. By processing the electric charge signals generated by these two piezoelectric elements, the number of times and the strength of the subject's swallowing are evaluated.

Patent Document 1: International Publication No. WO 2015/053241

BRIEF SUMMARY

However, there have been demands in recent years for improving the accuracy of measuring a person's swallowing ability using a swallowing sensor including the swallowing sensor disclosed in Patent Document 1.

The present disclosure provides a swallowing sensor capable of accurately measuring a person's swallowing ability and a swallowing ability diagnosis system provided with the same.

A swallowing sensor of the present disclosure is a swallowing sensor that is attached to a person's pharyngeal portion and that measures the person's swallowing ability, including: a film-shaped detector that detects vibration based on displacement and sound of the pharyngeal portion; an adhesive layer that is provided on one of two main sides of the detector and that attaches the detector to the pharyngeal portion; and a sensing film arranged on the detector to cover entirety of the other main side of the detector, wherein a main side of the sensing film that contacts the detector contains an adhesive component, the sensing film is attachable to the pharyngeal portion around the detector using the adhesive component, and the sensing film conveys vibration to the detector.

In addition, a swallowing ability diagnosis function system of the present disclosure includes the swallowing sensor, a controller that processes data of a detection result obtained by the swallowing sensor, and a determination unit that determines a person's swallowing ability on the basis of the data processed by the controller.

According to a swallowing sensor and a swallowing ability diagnosis system of the present disclosure, a person's swallowing ability can be more accurately measured.

BRIEF DESCRIPTION OF THE SEVERAL VIEWS OF THE DRAWINGS

These aspects and features of the present disclosure will become apparent from the following description in conjunction with embodiments with reference to the accompanying drawings.

DETAILED DESCRIPTION

Figure 1:
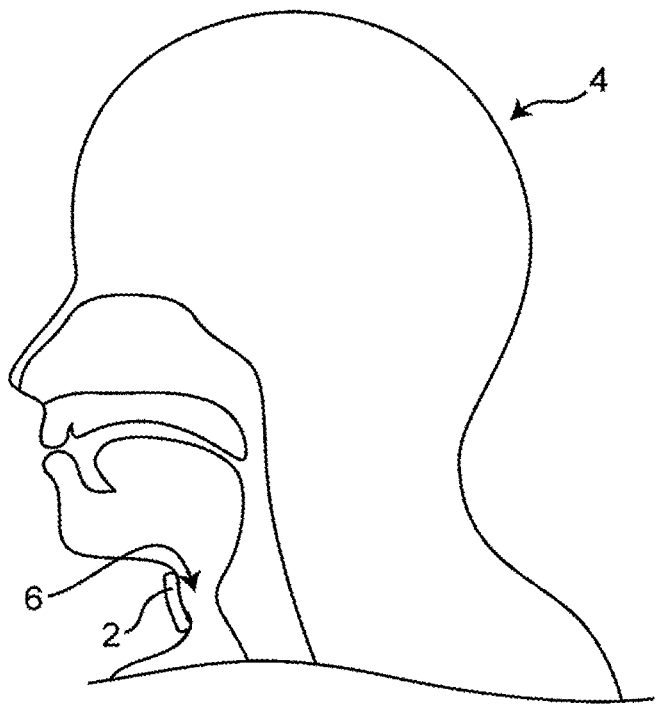
FIG. 1 is a schematic side view of a swallowing sensor in use according to an embodiment.

According to a first aspect of the present disclosure, there is provided a swallowing sensor that is attached to a person's pharyngeal portion and that measures the person's swallowing ability, including: a film-shaped detector that detects vibration based on displacement and sound of the pharyngeal portion; an adhesive layer that is provided on one of two main sides of the detector and that attaches the detector to the pharyngeal portion; and a sensing film arranged on the detector to cover entirety of the other main side of the detector, wherein a main side of the sensing film that contacts the detector contains an adhesive component, the sensing film is attachable to the pharyngeal portion around the detector using the adhesive component, and the sensing film conveys vibration to the detector. According to such a configuration, the detection accuracy of the swallowing sensor can be improved, and a person's swallowing ability can be accurately measured.

According to a second aspect of the present disclosure, there is provided the swallowing sensor according to the first aspect in which an adhesive force of the adhesive layer is greater than an adhesive force of the sensing film. By setting the adhesive force of the adhesive layer to be greater in this manner, the sensitivity of detecting vibration using the adhesive layer can be improved by improving the adhesion to the skin. Therefore, information obtained using the adhesive layer can be made more independent than information obtained using the sensing film, thereby realizing a desired detection form. Accordingly, the vibration detecting accuracy of the detector can be improved, and a person's swallowing ability can be accurately measured. Furthermore, by setting the adhesive force of the sensing film to be less than the adhesive force of the adhesive layer, the sensing film can be more easily peeled off without necessarily hurting the skin of the person when peeling off the sensing film.

According to a third aspect of the present disclosure, there is provided the swallowing sensor according to the first aspect or the second aspect in which Young's modulus of the adhesive layer is less than Young's modulus of the sensing film. By adjusting the Young's moduli in this manner, the ability to follow the stretching of pharyngeal skin can be made greater in the adhesive layer than in the sensing film, and the sensitivity of detecting vibration using the adhesive layer can be made greater. Therefore, information obtained using the adhesive layer can be made more independent than information obtained using the sensing film, thereby realizing a desired detection form.

Accordingly, the vibration detecting accuracy of the detector can be improved, and a person's swallowing ability can be more accurately measured.

According to a fourth aspect of the present disclosure, there is provided the swallowing sensor according to any one of the first to third aspects in which the sensing film includes a layer that contains the adhesive component and a base material that supports the layer. According to such a configuration, because the sensing film has the base material, vibration of a muscle around the thyroid cartilage can be more reliably conveyed to the detector, compared with the case in which the sensing film has no base material.

According to a fifth aspect of the present disclosure, there is provided the swallowing sensor according to any one of the first to fourth aspects in which a thickness of the sensing film is 90 μm or greater. According to such a configuration, because the thickness of the base material of the sensing film is made thicker, vibration of a muscle around the thyroid cartilage can be more reliably conveyed to the detector.

According to a sixth aspect of the present disclosure, there is provided the swallowing sensor according to any one of the first to fifth aspects in which the sensing film is made of polyethylene or polyester. According to such a configuration, the detection accuracy of the swallowing sensor can be improved, and a person's swallowing ability can be more accurately measured.

According to a seventh aspect of the present disclosure, there is provided the swallowing sensor according to any one of the first to sixth aspects in which the detector is a piezoelectric element that generates an electric charge signal on the basis of the detected vibration. By adopting a piezoelectric element in this manner, the detector can be realized with a simple configuration.

According to an eighth aspect of the present disclosure, there is provided the swallowing sensor according to the seventh aspect which further includes an amplifier circuit that amplifies an electric charge signal generated by the piezoelectric element. By adopting such an amplifier circuit, the detection result obtained by the swallowing sensor can be more easily evaluated.

According to a ninth aspect of the present disclosure, there is provided a swallowing ability diagnosis system including: the swallowing sensor according any one of the first to eighth aspects; a controller that processes data of a detection result obtained by the swallowing sensor; and a determination unit that determines the person's swallowing ability on the basis of the data processed by the controller. According to such a configuration, a person's swallowing ability can be accurately measured.

According to a tenth aspect of the present disclosure, there is provided a swallowing ability diagnosis system further including a respiratory condition detection device that detects a person's respiratory condition, wherein the determination unit determines the person's swallowing ability on the basis of the data processed by the controller and a detection result obtained by the respiratory condition detection device. According to such a configuration, a person's swallowing ability can be accurately measured.

According to an eleventh aspect of the present disclosure, there is provided a swallowing sensor that is attached to a person's pharyngeal portion and that measures the person's swallowing ability, including: a film-shaped detector that detects vibration based on displacement and sound of the pharyngeal portion; and an adhesive layer that is provided to cover entirety of one of two main sides of the detector and that attaches the detector to the pharyngeal portion. The length of the detector in the transverse direction is 5 mm or greater; the length of the detector in the longitudinal direction is 20 mm or greater; the length of the adhesive layer in the transverse direction is 30 mm or less; and the length of the adhesive layer in the longitudinal direction is 75 mm or less. According to such a configuration, the detection accuracy of the swallowing sensor can be improved, and a person's swallowing ability can be accurately measured.

According to a twelfth aspect of the present disclosure, there is provided the swallowing sensor according to the eleventh aspect which further includes a sensing film arranged on the detector to cover entirety of the other main side of the detector, wherein a main side of the sensing film that contacts the detector contains an adhesive component, the sensing film is attachable to the pharyngeal portion around the detector using the adhesive component, and the sensing film conveys vibration to the detector. According to such a configuration, because vibration can be conveyed to the detector not only using the adhesive layer but also using the sensing film, the detection accuracy of the swallowing sensor can be improved, and a person's swallowing ability can be accurately measured.

According to a thirteenth aspect of the present disclosure, there is provided the swallowing sensor according to the eleventh or twelfth aspect in which a horizontal width of the sensing film is 100 mm or less, and a vertical width of the sensing film is 75 mm or less. According to such a configuration, detection of noise of vibration can be suppressed, and furthermore the sensing film becomes more difficult to be peeled off.

According to a fourteenth aspect of the present disclosure, there is provided the swallowing sensor according to any one of the eleventh to thirteenth aspects in which the adhesive layer is capable of attaching the detector to the pharyngeal portion such that the center of the detector will be positioned at the pharyngeal bulge, which is a protrusion of the thyroid cartilage of the pharyngeal portion, and the transverse direction of the detector and the adhesive layer will coincide with the horizontal direction. According to such a configuration, advantageous effects obtained by specification of dimensions of the detector and the adhesive layer can be more effectively achieved.

According to a fifteenth aspect of the present disclosure, there is provided the swallowing sensor according to any one of the eleventh to fourteenth aspects in which the detector is a piezoelectric element that generates an electric charge signal on the basis of the detected vibration. By adopting a piezoelectric element in this manner, the detector can be realized with a simple configuration.

According to a sixteenth aspect of the present disclosure, there is provided the swallowing sensor according to the fifteenth aspect which further includes an amplifier circuit that amplifies an electric charge signal generated by the piezoelectric element. By adopting such an amplifier circuit, the detection result obtained by the swallowing sensor can be more easily evaluated.

According to a seventeenth aspect of the present disclosure, there is provided a swallowing ability diagnosis system including: the swallowing sensor according any one of the eleventh to sixteenth aspects; a controller that processes data of a detection result obtained by the swallowing sensor; and a determination unit that determines the person's swallowing ability on the basis of the data processed by the controller. According to such a configuration, a person's swallowing ability can be accurately measured.

According to an eighteenth aspect of the present disclosure, there is provided the swallowing ability diagnosis system according to the seventeenth aspect which further includes a respiratory condition detection device that detects a person's respiratory condition, wherein the determination unit determines the person's swallowing ability on the basis of the data processed by the controller and a detection result obtained by the respiratory condition detection device. According to such a configuration, a person's swallowing ability can be accurately measured.

Hereinafter, an embodiment of the present disclosure will be described in detail on the basis of the drawings.

Embodiment

Figure 2:
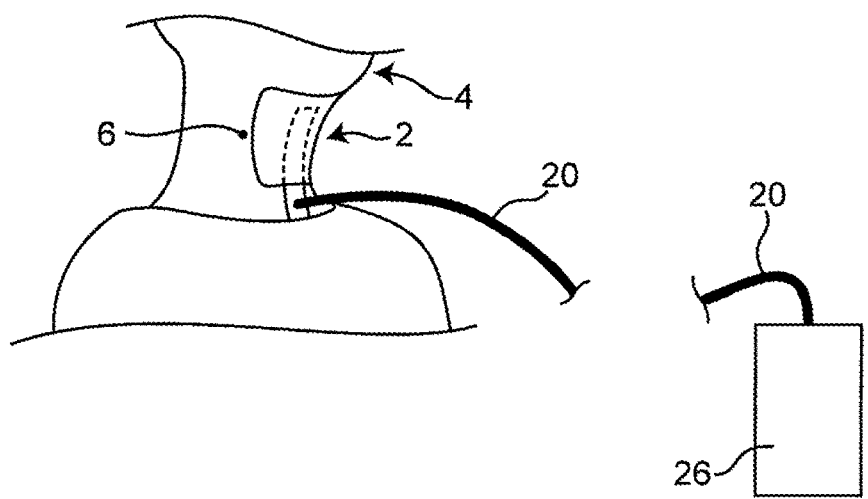
FIG. 2 is a schematic perspective view of the swallowing sensor in use.
Figure 3A:
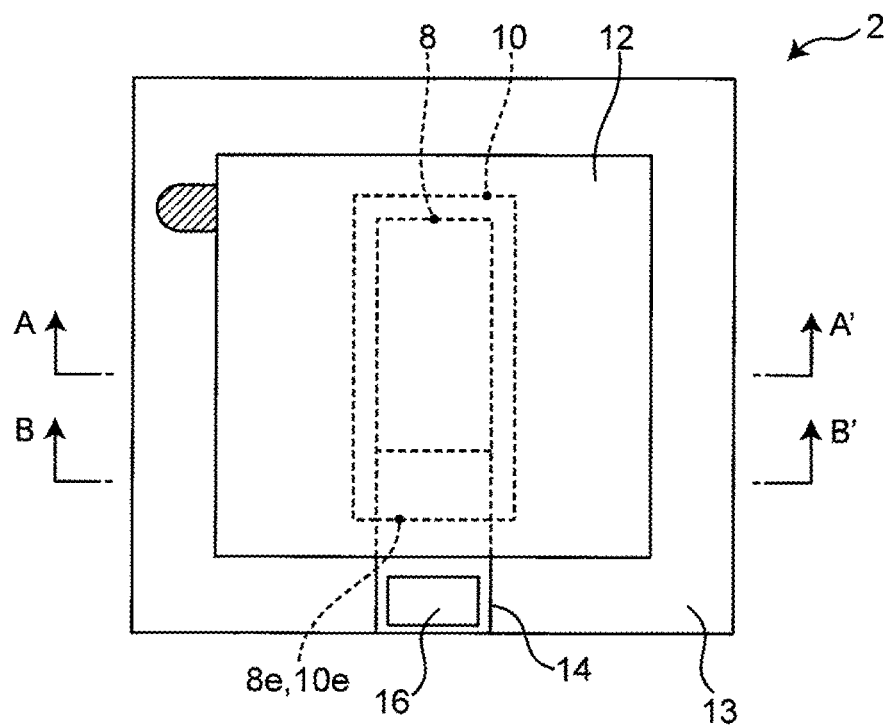
FIG. 3A is a front view of the swallowing sensor before use.
Figure 3B:
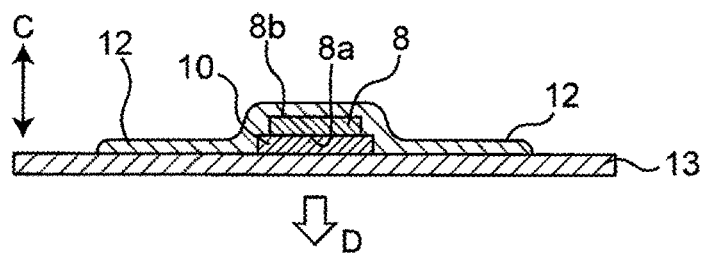
FIG. 3B is a cross-sectional view taken along line A-A' in FIG. 3A.
Figure 3C:
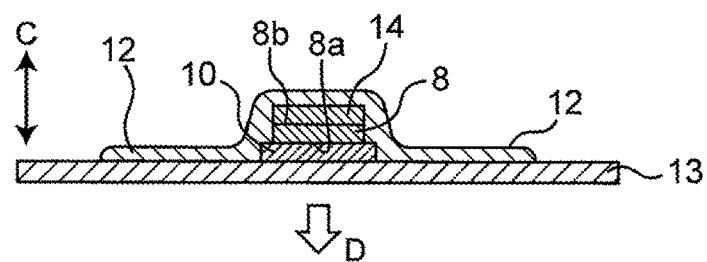
FIG. 3C is a cross-sectional view taken along line B-B' in FIG. 3A.

FIGS. 1 to 3 include diagrams illustrating the schematic configuration of a swallowing sensor 2 according to the embodiment. FIG. 1 is a schematic side view of the swallowing sensor 2 in use, and FIG. 2 is a schematic perspective view of the swallowing sensor 2 in use. FIG. 3A is a front view of the swallowing sensor 2 before use. FIG. 3B is a cross-sectional view taken along line A-A' in FIG. 3A, and FIG. 3C is a cross-sectional view taken along line B-B' in FIG. 3A.

As illustrated in FIGS. 1 and 2, the swallowing sensor 2 is a film-shaped sensor that is attached to a pharyngeal portion 6 of a person 4, who is a subject, and that is used to measure the swallowing ability of the person 4.

The swallowing sensor 2 includes, as illustrated in FIG. 3A, a detector 8, an adhesive layer 10, a sensing film 12, a separator 13, a substrate 14, and a connector 16. The swallowing sensor 2 has a multilayer structure obtained by stacking these elements in a thickness direction C (FIGS. 3B and 3C). Specifically, on the cross section taken along line A-A', as illustrated in FIG. 3B, the sensing film 12, the detector 8, the adhesive layer 10, and the separator 13 are stacked in this order from top to bottom. On the cross section taken along line B-B', as illustrated in FIG. 3C, the sensing film 12, the substrate 14, the detector 8, the adhesive layer 10, and the separator 13 are laminated/stacked in this order from top to bottom.

At the time of attaching the swallowing sensor 2 to the pharyngeal portion 6, the separator 13 is peeled off from the swallowing sensor 2, and the adhesive side of the adhesive layer 10 and the sensing film 12, which adhered to the separator 13, is attached to the pharyngeal portion 6. In FIGS. 3B and 3C, a direction in which the swallowing sensor 2 is attached to the pharyngeal portion 6 is referred to as an attaching direction D. Hereinafter, each configuration of the swallowing sensor 2 will be described.

The detector 8 is a member for detecting vibration of the pharyngeal portion 6 that occurs accompanying to the swallowing operation of the person 4. The detector 8 of the present embodiment is a piezoelectric element that generates an electric charge signal on the basis of the detected vibration. The detector 8 is not limited to a piezoelectric element, and the detector 8 may be anything, such as a strain gauge, as long as the detector 8 is capable of detecting vibration by calculating changes of electrical characteristics over time due to displacement or distortion.

The detector 8 of the present embodiment is a thin-film-shaped sensor and is formed in a vertically-long rectangular shape in plan view, as illustrated in FIG. 3A. As illustrated in FIG. 3B, the detector 8 has two main sides 8a and 8b, which face each other in the thickness direction C. The adhesive layer 10 is adhered to the main side 8a, which is closer to the pharyngeal portion 6 (lower side). The sensing film 12 is adhered to the main side 8b, which is farther from the pharyngeal portion 6 (upper side), on the cross section taken along line A-A', and the substrate 14 is connected to the main side 8b on the cross section taken along line B-B'.

The detector 8 of the present embodiment is configured to detect vibration in the center of the pharyngeal portion 6 using the adhesive layer 10, and to detect vibration in the peripheral part of the pharyngeal portion 6 using the sensing film 12.

The adhesive layer 10 is a member that attaches the detector 8 to the pharyngeal portion 6 and that conveys vibration of the pharyngeal portion 6 to the detector 8. The adhesive layer 10 of the present embodiment is configured such that both sides thereof in the thickness direction C are sticky (such as a double-sided adhesive tape). In a state before use illustrated in FIG. 3B, the adhesive layer 10 is adhered to both the detector 8 and the separator 13.

As illustrated in FIG. 3A, the adhesive layer 10 is, like the detector 8, rectangular in plan view, and has external dimensions slightly larger than the detector 8. On the lower side of the page of FIG. 3A, an end portion 10e of the adhesive layer 10 coincide with an end portion 8e of the detector 8. As illustrated in FIG. 3A, it is only necessary for the adhesive layer 10 to be provided to cover the entirety of the main side 8a, which is one of two main sides of the detector 8.

Figure 4:
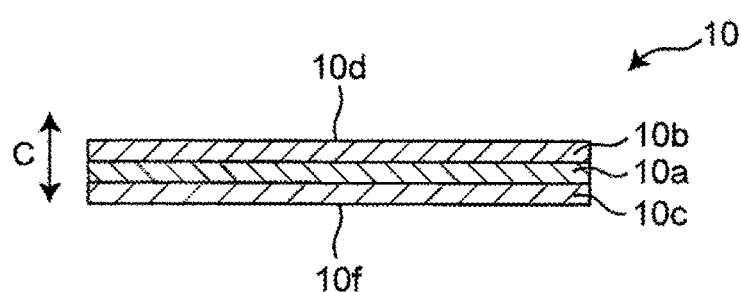
FIG. 4 is a vertical cross-sectional view of an adhesive layer.

FIG. 4 is a vertical cross-sectional view of the adhesive layer 10. As illustrated in FIG. 4, the adhesive layer 10 includes a base material 10a, a first layer 10b, and a second layer 10c, and the first layer 10b and the second layer 10c are arranged to sandwich the base material 10a from both sides. The base material 10a is a layer that supports the first layer 10b and the second layer 10c. The base material 10a has certain stiffness and is configured to more reliably convey the vibration of the pharyngeal portion 6 to the detector 8. The first layer 10b and the second layer 10c are layers that contain adhesive components arranged on both sides of the base material 10a. In the first layer 10b and the second layer 10c, sides that are exposed without necessarily contacting the base material 10a are adhesive sides 10d and 10f. In the present embodiment, the thickness of the base material 10a is set to be less than the sum of the thickness of the first layer 10b and the second layer 10c. For example, the thickness of the base material 10a is set to 25 µm, and the sum of the thickness of the first layer 10b and the second layer 10c is set to 75 µm. In addition, the material of the base material 10a is, for example, polyethylene, and the material of the first layer 10b and the second layer 10c is, for example, a composition containing a rubber base, such as a synthetic polyisoprene rubber or a styrene-isoprene-styrene block copolymer, blended with a tackifier resin, a softener, or the like. However, there is no particular restriction on the material of the base material 10a, the first layer 10b, and the second layer 10c.

Referring back to FIG. 3, the sensing film 12 is, like the adhesive layer 10, a member that attaches the detector 8 to the pharyngeal portion 6 and that conveys vibration of the pharyngeal portion 6 to the detector 8. The sensing film 12 of the present embodiment is a single-sided adhesive tape. A main side of the sensing film 12 facing toward the attaching direction D (contacting the detector 8) has an adhesive component to configure an adhesive side. The sensing film 12 is adhered to the detector 8 and the separator 13 on the cross section taken along line A-A' and is adhered to the substrate 14 and the separator 13 on the cross section taken along line B-B'. As illustrated in FIG. 3A, the sensing film 12 has a substantially rectangular shape that covers the entirety of the detector 8 and the adhesive layer 10 in plan view. The sensing film 12 is provided to cover the entirety of the main side 8b (FIG. 3B), which is the other main side of the detector 8. The sensing film 12 is adhered to the separator 13 around the detector 8 and the adhesive layer 10 in a direction along the surface of the swallowing sensor 2 (a direction along a plane perpendicular to the thickness direction C).

Figure 5:
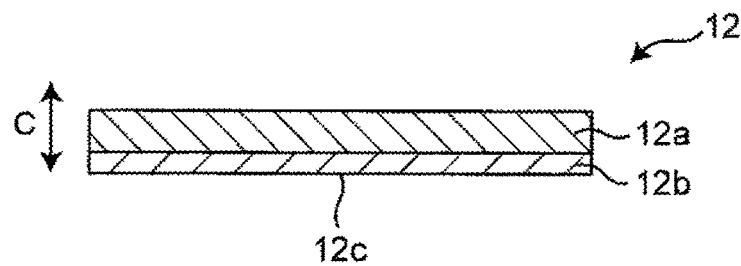
FIG. 5 is a vertical cross-sectional view of a sensing film.

FIG. 5 is a vertical cross-sectional view of the sensing film 12. As illustrated in FIG. 5, the sensing film 12 includes a base material 12a, and a layer 12b containing an adhesive component arranged on one of two main sides of the base material 12a. The base material 12a is a layer that supports the layer 12b containing an adhesive component. Like the base material 10a of the adhesive layer 10, the base material 12a has certain stiffness, and is configured to more reliably convey the vibration of the pharyngeal portion 6 to the detector 8. In the layer 12b, a side that is exposed without necessarily contacting the base material 12a is an adhesive side 12c. In the present embodiment, the thickness of the base material 12a is set to be greater than the thickness of the layer 12b. For example, the thickness of the base material 12a is set to 90 µm, and the thickness of the layer 12b is set to 40 µm. In addition, the material of the base material 12a is, for example, polyethylene, and the material of the layer 12b is, for example, an acrylic material (such as an acrylic acid ester monomer polymer).

The above-described adhesive layer 10 and sensing film 12 have the function of adhesively fixing the detector 8 to the pharyngeal portion 6. In the present embodiment, the adhesive force and Young's modulus are made different between the adhesive layer 10 and the sensing film 12. Specifically, the adhesive force of the adhesive layer 10 is set to be greater than the adhesive force of the sensing film 12. In addition, the Young's modulus of the adhesive layer 10 is set to be less than the Young's modulus of the sensing film 12. That is, the degree of extensibility of the adhesive layer 10 is set to be greater than the degree of extensibility of the sensing film 12. Note that the adhesive force is a force necessary for peeling off an item that has been stuck and may be defined as a force that occurs in response to contact between the adhesive side and the adherend. In addition, the Young's modulus can be obtained as a stress/strain ratio. The relationship between the adhesive force and the Young's modulus of the adhesive layer 10 and the sensing film 12 and the relationship between the vibration and the measurement sensitivity will be described later.

The separator 13 is a member that holds the swallowing sensor 2 before the swallowing sensor 2 is attached to the pharyngeal portion 6. An adhesive side 10f of the adhesive layer 10 and the adhesive side 12c of the sensing film 12 are adhered to the surface of the separator 13. When the separator 13 is peeled off from the adhesive layer 10 and the sensing film 12, it becomes possible to attach the swallowing sensor 2 to the pharyngeal portion 6 using the adhesive side 10f of the adhesive layer 10 and the adhesive side 12c of the sensing film 12.

The substrate 14 is a substrate for amplifying and converting an electric charge signal generated by the detector 8 on the basis of the vibration of the pharyngeal portion 6. The substrate 14 is connected to one of two end portions of the detector 8 (the lower side of the page of FIG. 3A) and is held between the detector 8 and the sensing film 12 in the thickness direction C (FIG. 3C). The substrate 14 has the connector 16, and a cord 20 (FIG. 2) is connected to the connector 16. The substrate 14 is electrically coupled to a controller 26 (FIG. 2) with the connector 16 and the cord 20 interposed therebetween. The substrate 14 generates a certain digital signal by amplifying and converting an electric charge signal generated by the detector 8, and outputs the digital signal to the controller 26. The controller 26 is one that processes data of a detection result obtained by the swallowing sensor 2 by processing the digital signal output from the substrate 14, and includes, for example, a microcomputer. Processing performed by the controller 26 is processing such as outputting data for enabling diagnosis of the swallowing ability of the person 4.

Figure 6:
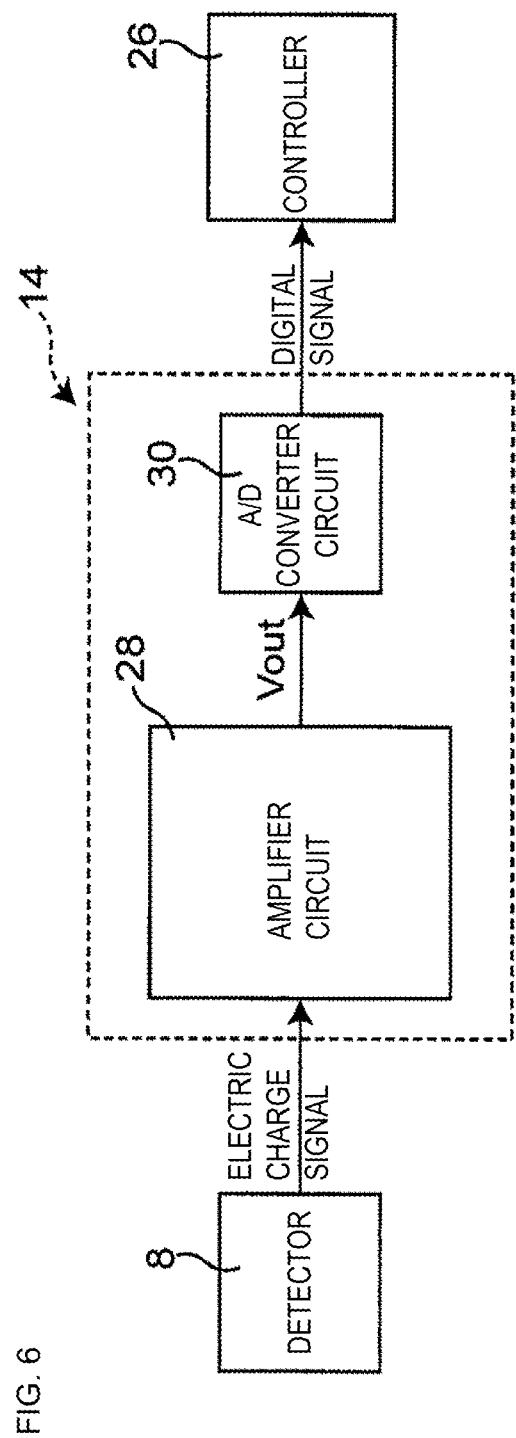
FIG. 6 is a block diagram representing the schematic configuration of a substrate.

FIG. 6 is a block diagram representing the schematic configuration of the substrate 14. As illustrated in FIG. 6, the substrate 14 includes an amplifier circuit 28 and an A/D converter circuit 30, which serve as a configuration connected between the detector 8 and the controller 26.

The amplifier circuit 28 is an amplifier circuit for converting an electric charge signal transmitted from the detector 8 to a voltage signal Vout. The A/D converter circuit 30 is a circuit for converting the voltage signal Vout from an analog signal to a digital signal. The digital signal output from the A/D converter circuit 30 is output to the controller 26. On the basis of the digital signal output from the substrate 14, the controller 26 displays a measurement result regarding the motion of the pharyngeal portion 6 that occurs accompanying to the swallowing operation of the person 4.

The electric charge signal transmitted from the detector 8 includes an electric charge signal based on vibration due to "displacement" and an electric charge signal based on vibration due to "sound". The frequency of an electric charge signal based on vibration due to "displacement" is, for example, 100 mHz to 10 Hz, and the frequency of an electric charge signal based on vibration due to "sound" is, for example, 100 Hz to 10 kHz. Because the frequency bands of the electric charge signals belong to different ranges, the substrate 14 conducts filtering based on the frequency bands, thereby separately outputting a measurement result based on vibration due to "displacement" and a measurement result based on vibration due to "sound". Although various methods are adoptable as the filtering method, a description thereof will be omitted in the present specification.

A method of using and the operation of the swallowing sensor 2 with the foregoing configuration will be described.

At first, a health professional peels off the separator 13 from the adhesive side 10f of the adhesive layer 10 and the adhesive side 12c of the sensing film 12. Holding the swallowing sensor 2 from which the separator 13 has been peeled off, the health professional attaches the adhesive side 10f of the adhesive layer 10 and the adhesive side 12c of the sensing film 12 to the pharyngeal portion 6.

Figure 7:
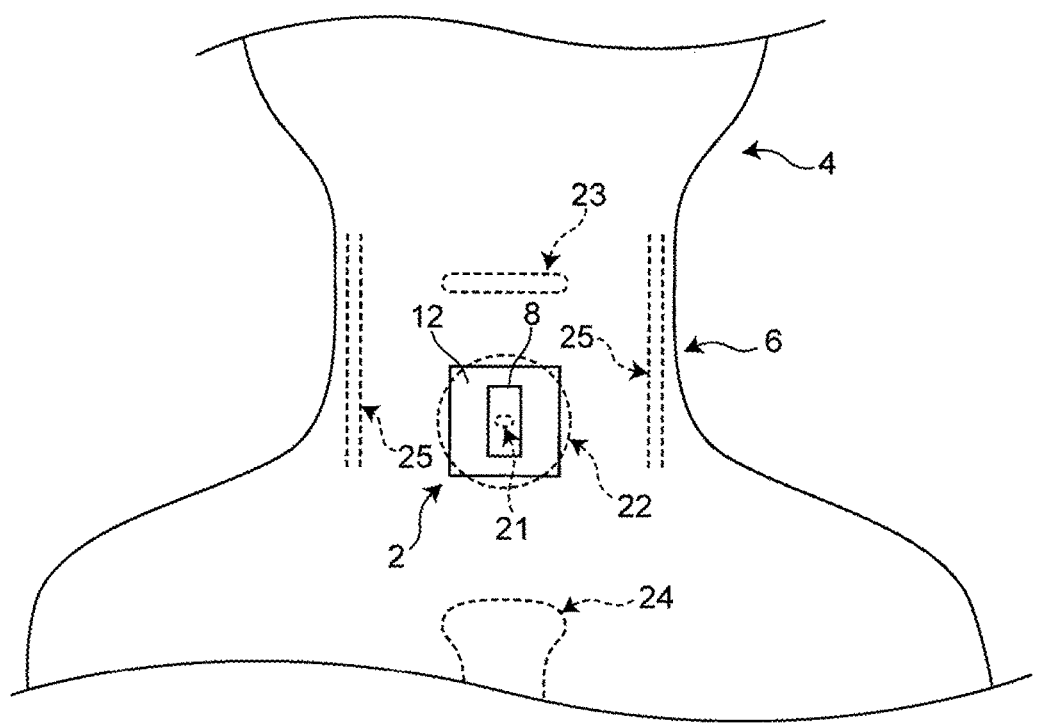
FIG. 7 is a front view illustrating the swallowing sensor after being attached.

FIG. 7 illustrates an example of the swallowing sensor 2 after being attached to the pharyngeal portion 6. As illustrated in FIG. 7, the swallowing sensor 2 is placed such that the center of the detector 8 will coincide with the pharyngeal bulge, which is a protrusion of a thyroid cartilage 21 of the pharyngeal portion 6. At this time, the swallowing sensor 2 is placed such that the transverse direction of the detector 8 and the adhesive layer 10 will coincide with the horizontal direction, and the longitudinal direction thereof will coincide with the vertical direction.

Note that there may be some errors in the attachment position and angle of the swallowing sensor 2.

A thyropharyngeal muscle 22, which supports the thyroid cartilage 21 from the back, is positioned around the thyroid cartilage 21. The sensing film 12 is arranged to substantially cover the thyropharyngeal muscle 22. A hyoid bone 23 is positioned above the thyroid cartilage 21 and the thyropharyngeal muscle 22, and a sternum 24 is positioned below the thyroid cartilage 21 and the thyropharyngeal muscle 22. A pair of carotid arteries 25 is positioned on both the left and right sides of the thyroid cartilage 21 and the thyropharyngeal muscle 22. The sensing film 12 is arranged in a range that overlaps none of the hyoid bone 23, the sternum 24, and the carotid arteries 25.

In one swallowing operation, the thyroid cartilage 21 and the hyoid bone 23 move vertically in an interlocking manner, and the thyropharyngeal muscle 22 also moves at the same time. Specifically, in one swallowing operation, the thyroid cartilage 21 and the hyoid bone 23 move upward, and then move downward for the same distance to return to the same positions. At this time, the movement of the thyroid cartilage 21 and vibration involved in the motion of the thyropharyngeal muscle 22 are conveyed by the adhesive layer 10 and the sensing film 12 to the detector 8. In the swallowing sensor 2 of the present embodiment, the adhesive layer 10 is provided at a position that substantially overlaps the detector 8, and the sensing film 12 is provided around the adhesive layer 10, thereby attaching the swallowing sensor 2 to the pharyngeal portion 6. According to such a configuration, while conveying mainly vibration of the thyroid cartilage 21 to the detector 8 using the adhesive layer 10, mainly vibration of the thyropharyngeal muscle 22 can be conveyed to the detector 8 using the sensing film 12.

In this manner, not only detection of vibration of the pharyngeal portion 6 using the adhesive layer 10, but also conveying of vibration of the pharyngeal portion 6 around the adhesive layer 10 to the detector 8 using the sensing film 12 enables detection of vibration of the pharyngeal portion 6 in a wide range. That is, it becomes possible to detect vibration of the thyroid cartilage 21, positioned at the center of the pharyngeal portion 6, using the adhesive layer 10, and to detect vibration of the thyropharyngeal muscle 22 around the thyroid cartilage 21 using the sensing film 12. According to such a method, the swallowing ability of the person 4 can be more accurately measured, compared with the case of detecting vibration of the pharyngeal portion 6 using only the adhesive layer 10. Furthermore, at the time of attaching the swallowing sensor 2 to the pharyngeal portion 6, the detector 8 becomes more difficult to be peeled off from the pharyngeal portion 6 by attaching the swallowing sensor 2 to the pharyngeal portion 6 using the sensing film 12 in addition to the adhesive layer 10. Accordingly, the detection accuracy of the detector 8 can be improved, and the swallowing ability of the person 4 can be more accurately measured.

Here, two types of vibrations, one based on "displacement" and the other based on "sound", occur in the thyroid cartilage 21 and the thyropharyngeal muscle 22. In measuring the swallowing ability, these two types of vibrations can be detected. However, because the thyropharyngeal muscle 22 is close to the carotid arteries 25 and other blood vessels, vibration regarding sound contains many noise components. Because of this point, for the thyroid cartilage 21, the accuracy of detecting vibration based on both "displacement" and "sound" can be increased, and, for the thyropharyngeal muscle 22, the accuracy of detecting vibration based on "displacement" can be mainly increased.

To more accurately realize such a detection form, in the present embodiment, the adhesive force and Young's modulus are made different between the adhesive layer 10 and the sensing film 12. Specifically, the adhesive force of the adhesive layer 10 is set to be greater than the adhesive force of the sensing film 12. By setting the adhesive force of the adhesive layer 10 to be greater, the sensitivity of detecting vibration using the adhesive layer 10 can be improved by improving the adhesion to the skin. Accordingly, information obtained using the adhesive layer 10 can be made more independent than information obtained using the sensing film 12. According to such a configuration, the following method becomes possible: detecting vibration based on displacement of the thyropharyngeal muscle 22, which is necessary around the thyroid cartilage 21, while improving the sensitivity of detecting vibration based on displacement and sound of the thyroid cartilage 21 and suppressing picking up of noise of pulsation of blood vessels or the like. Accordingly, the vibration detecting accuracy of the detector 8 can be improved, and the swallowing ability of the person 4 can be more accurately measured.

In addition, the Young's modulus of the adhesive layer 10 is set to be less than the Young's modulus of the sensing film 12 in the present embodiment. By adjusting the Young's moduli in this manner, the ability to follow the stretching of skin of the pharyngeal portion 6 can be made greater in the adhesive layer 10 than in the sensing film 12, and the sensitivity of detecting vibration using the adhesive layer 10 can be made greater. Accordingly, information obtained using the adhesive layer 10 can be made more independent than information obtained using the sensing film 12. Therefore, the following method becomes possible: detecting vibration based on displacement of the thyropharyngeal muscle 22, which is necessary around the thyroid cartilage 21, while improving the sensitivity of detecting vibration based on displacement and sound of the thyroid cartilage 21 and suppressing picking up of noise of pulsation of blood vessels or the like. Accordingly, the vibration detecting accuracy of the detector 8 can be improved, and the swallowing ability of the person 4 can be more accurately measured.

In addition, in the present embodiment, the adhesive layer 10 and the sensing film 12 both have base materials with certain stiffness. Because the adhesive layer 10 has the base material 10a and the sensing film 12 has the base material 12a as described above, vibration of the thyroid cartilage 21 and vibration of the thyropharyngeal muscle 22 can be more reliably conveyed to the detector 8.

After that, when the measurement is completed, the swallowing sensor 2 is detached from the pharyngeal portion 6. As has been described above, because the adhesive force of the sensing film 12 is set to be less than the adhesive force of the adhesive layer 10, the sensing film 12 can be more easily peeled off without necessarily hurting the skin of the person 4 when peeling off the sensing film 12, which occupies a wide range.

Next, the results of simulations conducted using the swallowing sensor 2 of the present embodiment will be described using FIGS. 8 to 10. FIGS. 8 to 10 are the results of simulations for comparing the characteristics of particularly the sensing film 12 in the swallowing sensor 2. In these simulations, experiments were conducted using the swallowing sensor 2 and a swallowing simulator (not illustrated). The swallowing simulator is a machine capable of simulating the swallowing operation of the person 4, and this machine can repeatedly replicate the same swallowing operation. The experiments were conducted by attaching the swallowing sensor 2 to the surface of the swallowing simulator. FIGS. 8 to 10 are data representing the displacement of the intensity of a signal over time, which is output to the controller 26 on the basis of one swallowing operation under respective conditions. Note that data is illustrated which is obtained by performing filtering based on the above-mentioned frequency bands to extract the signal intensity mainly related to "displacement", out of "displacement" and "sound".

Figure 8A:
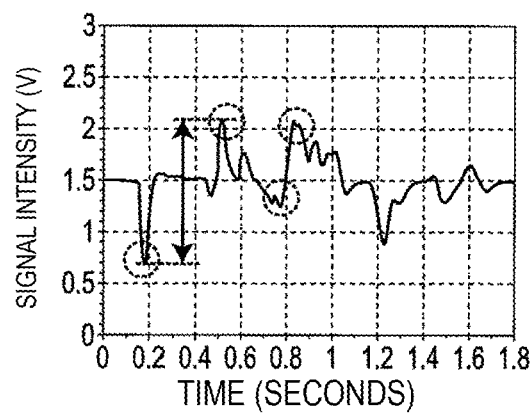
FIG. 8A is a graph illustrating the result of a simulation of the swallowing sensor.
Figure 8B:
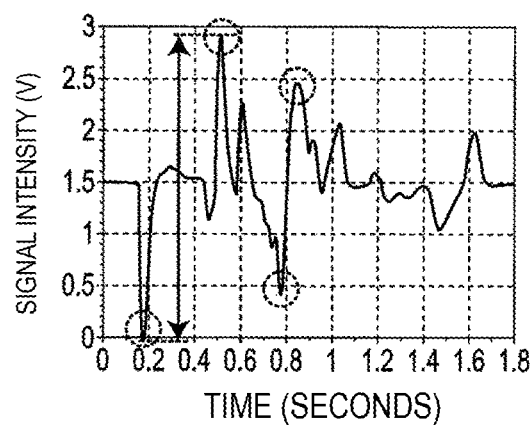
FIG. 8B is a graph illustrating the result of a simulation of the swallowing sensor.

FIGS. 8A and 8B are the results of simulations comparing the presence/absence of the sensing film 12. FIG. 8A is the result of a simulation (comparative example) using a swallowing sensor not provided with the sensing film 12. FIG. 8B is the result of a simulation (first example) using the swallowing sensor 2 provided with the sensing film 12. Comparison of the results in FIGS. 8A and 8B makes it clear that the difference between the minimum point and the maximum point of the signal intensity is greater in the first example than in the comparative example. The peaks and valleys of other representative amplitudes (circular portions surrounded by dotted lines) are also greater in the first example than in the comparative example. Accordingly, it is clear that the greater signal intensity is output in the first example, and the vibration detecting sensitivity is higher. That is, it is clear that the vibration detecting sensitivity increases by having the sensing film 12. Note that, in the swallowing sensor 2 of the present embodiment, the amplitude of a signal is amplified by providing the amplifier circuit 28 on the substrate 14. As illustrated in FIGS. 8A and 8B, the vibration detecting sensitivity can be greatly improved by providing the sensing film 12. In such a case, there may be an advantageous effect that the amplifier circuit 28 can be omitted.

Figure 9A:
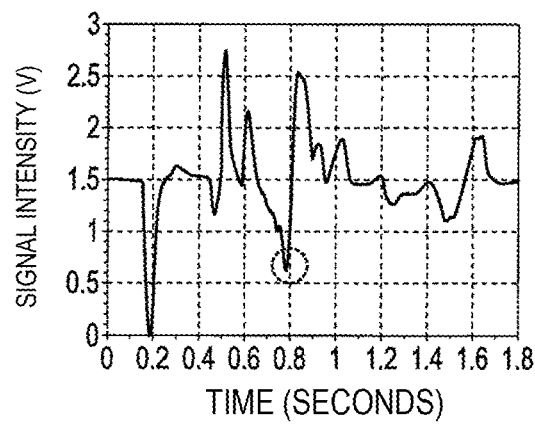
FIG. 9A is a graph illustrating the result of a simulation of the swallowing sensor.
Figure 9B:
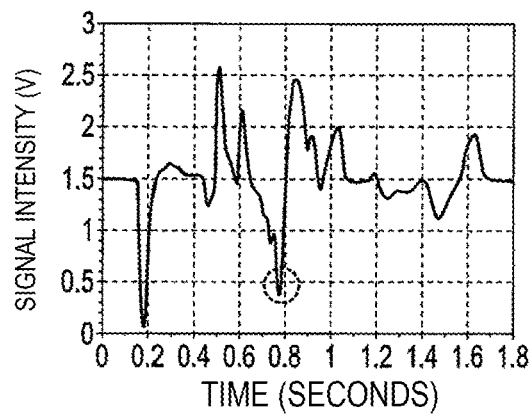
FIG. 9B is a graph illustrating the result of a simulation of the swallowing sensor.
Figure 9C:
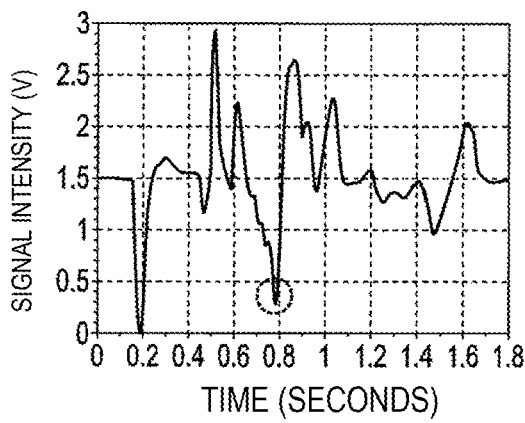
FIG. 9C is a graph illustrating the result of a simulation of the swallowing sensor.
Figure 9D:
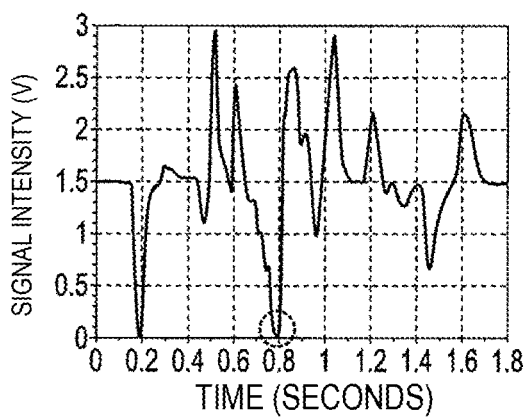
FIG. 9D is a graph illustrating the result of a simulation of the swallowing sensor.

FIGS. 9A and 9D are the results of simulations comparing the thickness of the base material 12a of the sensing film 12. FIG. 9A is the result of a simulation (second example) using the swallowing sensor 2 in which the thickness of the base material 12a of the sensing film 12 is 45 µm. FIG. 9B is the result of a simulation (third example) using the swallowing sensor 2 in which the thickness of the base material 12a of the sensing film 12 is 75 µm. FIG. 9C is the result of a simulation (fourth example) using the swallowing sensor 2 in which the thickness of the base material 12a of the sensing film 12 is 90 µm. FIG. 9D is the result of a simulation (fifth example) using the swallowing sensor 2 in which the thickness of the base material 12a of the sensing film 12 is 125 µm. Comparison of the results in FIGS. 9A to 9D makes it clear that, regarding the valleys of representative amplitudes (circular portions surrounded by dotted lines), the greater signal intensity is output in the fourth and fifth examples, where the thickness of the base material 12a of the sensing film 12 is thicker, than in the second and third examples, and it is clear that the vibration detecting sensitivity is higher. In addition, comparison on the results in FIGS. 9C and 9D makes it clear that the greater signal intensity is output in the fifth example, where the thickness of the base material 12a of the sensing film 12 is thicker, than in the fourth example, and it is clear that the vibration detecting sensitivity is higher. From these results, it is clear that the vibration detecting sensitivity can be increased by setting the thickness of the base material 12a of the sensing film 12 to 90 µm or greater.

Figure 10A:
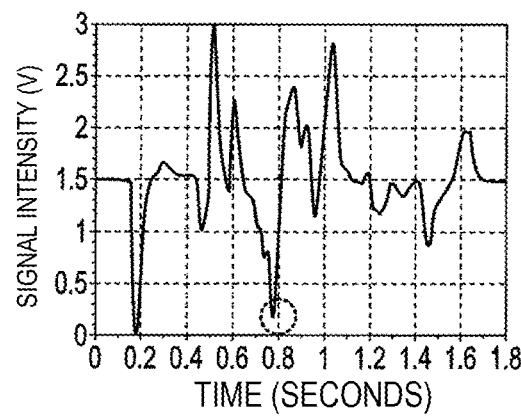
FIG. 10A is a graph illustrating the result of a simulation of the swallowing sensor.
Figure 10B:
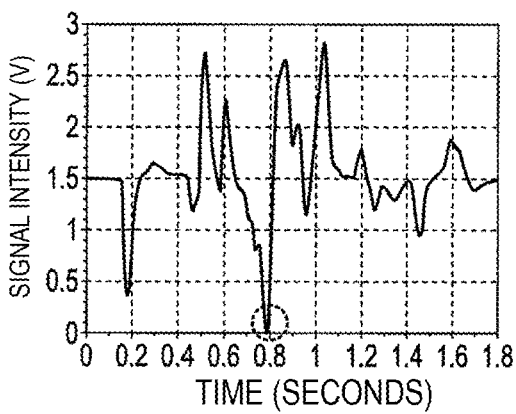
FIG. 10B is a graph illustrating the result of a simulation of the swallowing sensor.
Figure 10C:
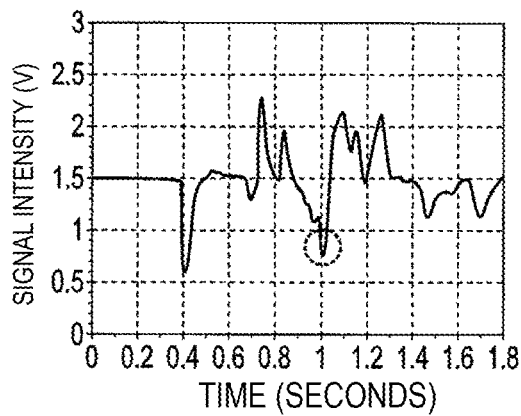
FIG. 10C is a graph illustrating the result of a simulation of the swallowing sensor.

FIGS. 10A to 10C are the results of simulations comparing the material of the base material 12a of the sensing film 12. FIG. 10A is the result of a simulation (sixth example) using the swallowing sensor 2 in which the material of the base material 12a of the sensing film 12 is polyethylene. FIG. 10B is the result of a simulation (seventh example) using the swallowing sensor 2 in which the material of the base material 12a of the sensing film 12 is polyester. FIG. 10C is the result of a simulation (eighth example) using the swallowing sensor 2 in which the material of the base material 12a of the sensing film 12 is polyurethane. Comparison of the results in FIGS. 10A to 10C makes it clear that, regarding the valleys of representative amplitudes (circular portions surrounded by dotted lines), the greater signal intensity is output in the sixth and seventh examples than in the eighth example, and it is clear that the vibration detecting sensitivity is higher. From the results, it is clear that the vibration detecting sensitivity can be increased by using polyethylene or polyester for the material of the base material 12a of the sensing film 12.

Next, the dimensions of the swallowing sensor 2 will be described using FIG. 11.

Figure 11:
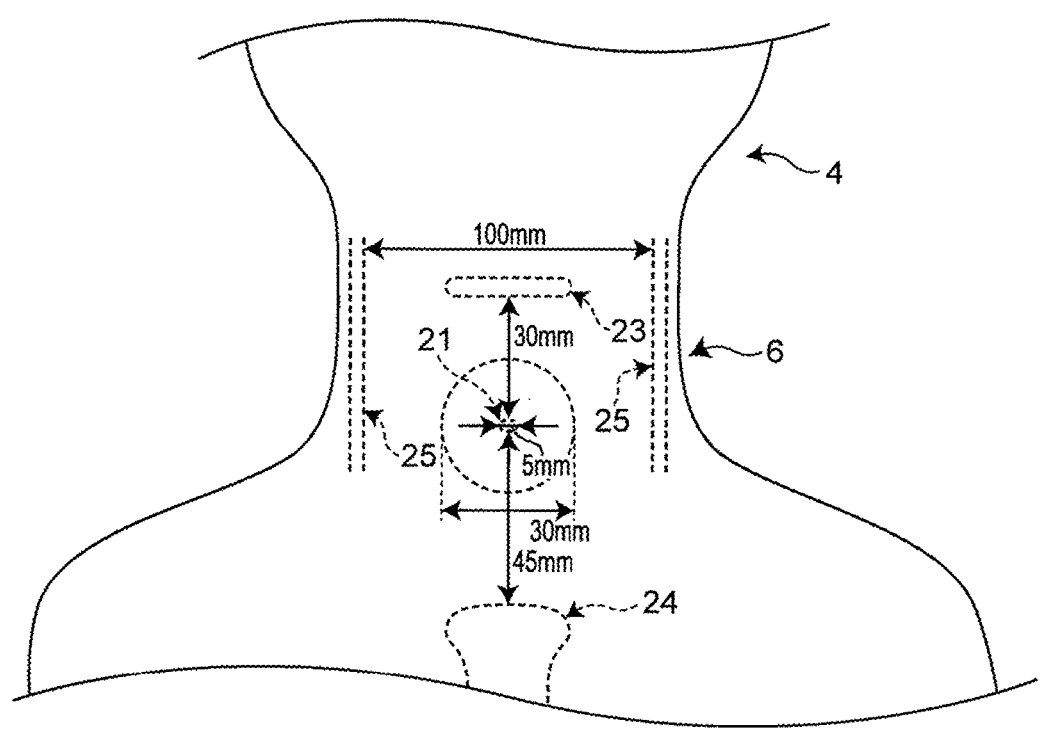
FIG. 11 is a front view illustrating the dimensions of a pharyngeal portion.

FIG. 11 is a front view illustrating the arrangement relationship and dimensions of the bones, muscles, blood vessels, and the like in the pharyngeal portion 6 of the person 4. As illustrated in FIG. 11, the thyroid cartilage 21 has a width of about 5 mm in the horizontal direction. The distance from the thyroid cartilage 21 up to the hyoid bone 23 is about 30 mm. The distance from the thyroid cartilage 21 down to the sternum 24 is about 45 mm. The thyropharyngeal muscle 22, which is positioned surrounding the thyroid cartilage 21, occupies an area around the thyroid cartilage 21 in plan view, and has a width of about 30 mm in the horizontal direction. The relative distance between the carotid arteries 25, which are arranged on the left and right of the thyropharyngeal muscle 22, is about 100 mm. In one swallowing operation, the thyroid cartilage 21 and the hyoid bone 23 move upward for about 20 mm from the positions indicated in FIG. 11, and then move downward for the same distance to return to the original positions.

In such a configuration, the swallowing sensor 2 is placed such that the center of the detector 8 will overlap the pharyngeal bulge, which is a protrusion of the thyroid cartilage 21, and the transverse direction of the detector 8 will coincide with the vertical direction. Assuming such an arrangement, the horizontal width, that is, the width in the transverse direction, of the detector 8 is set to be 5 mm or greater. Accordingly, the detector 8 can cover the width direction of the thyroid cartilage 21, and vibration based on displacement and sound of the thyroid cartilage 21 can be more accurately detected. In addition, the vertical width, that is, the width in the longitudinal direction, of the detector 8 is set to be 20 mm or greater. Accordingly, the detector 8 can at least partially cover the vertical movement of the thyroid cartilage 21 accompanying the swallowing operation, and vibration based on displacement and sound of the thyroid cartilage 21 can be more accurately detected. In addition, the width in the transverse direction of the adhesive layer 10 is set to be 30 mm or less. Accordingly, the horizontal width of the adhesive layer 10 becomes less than the width of the thyropharyngeal muscle 22. In the horizontal direction, curvature of the skin is greatly different between the thyropharyngeal muscle 22 and its outside portion. Thus, curvature of the adhesive layer 10 can be suppressed to be small by making the horizontal width of the adhesive layer 10 less than the width of the thyropharyngeal muscle 22, and the adhesive layer 10 becomes more difficult to be peeled off from the pharyngeal portion 6. Furthermore, the width in the longitudinal direction of the adhesive layer 10 is set to be 75 mm or less. Accordingly, because the adhesive layer 10 can be arranged not overlapping the hyoid bone 23 and the sternum 24 in the vertical direction, detection of noise of vibration can be suppressed, and furthermore the adhesive layer 10 becomes more difficult to be peeled off.

In the configuration of the above-mentioned detector 8, the swallowing ability can be diagnosed in a mode not provided with the sensing film 12. Note that the swallowing ability can be further accurately diagnosed by providing the sensing film 12 in the following modes.

In the configuration of the above-mentioned detector 8, the horizontal width of the sensing film 12 is set to be 100 mm or less. Accordingly, because the sensing film 12 can fit in a range not overlapping the carotid arteries 25, detection of noise of vibration caused by pulsation of the carotid arteries 25 can be suppressed, thereby improving the detection accuracy. In addition, the vertical width of the sensing film 12 is set to be 75 mm or less. Accordingly, like the adhesive layer 10, because the sensing film 12 can be arranged not overlapping the hyoid bone 23 and the sternum 24 in the vertical direction, detection of noise of vibration can be suppressed, and furthermore the sensing film 12 becomes more difficult to be peeled off.

Figure 12:
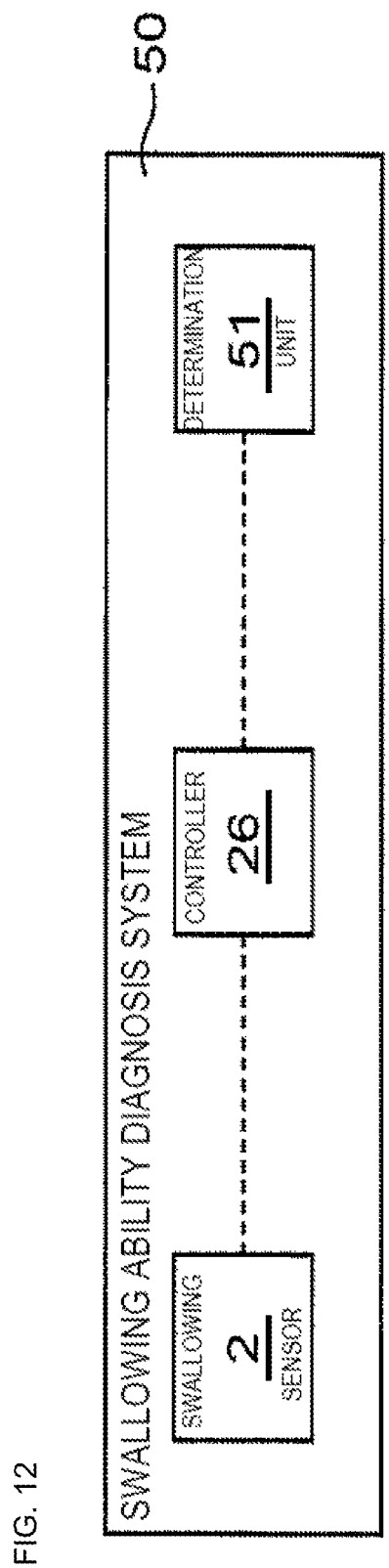
FIG. 12 is a block diagram representing the schematic configuration of a swallowing ability diagnosis system according to the embodiment.

Next, a swallowing ability diagnosis system 50 for diagnosing the swallowing ability of the person 4 using the swallowing sensor 2 will be described using FIG. 12. FIG. 12 illustrates the swallowing ability diagnosis system 50 according to the present embodiment. The swallowing ability diagnosis system 50 further includes, in addition to the above-described swallowing sensor 2 and controller 26, a determination unit 51 for determining (diagnosing) the swallowing ability of the person 4. The determination unit 51 is electrically coupled to the controller 26, and includes, for example, a microcomputer. As illustrated in FIG. 12, the swallowing sensor 2, the controller 26, and the determination unit 51 are connected in series. The determination unit 51 determines (diagnoses) the swallowing ability of the person 4 by processing data of a measurement result obtained by the swallowing sensor 2, which is output from the controller 26. According to such a configuration, the swallowing ability of the person 4 can be accurately diagnosed using the above-described swallowing sensor 2. Note that various methods can be adopted as a method of processing data by the determination unit 51, that is, a specific determination method.

Figure 13:
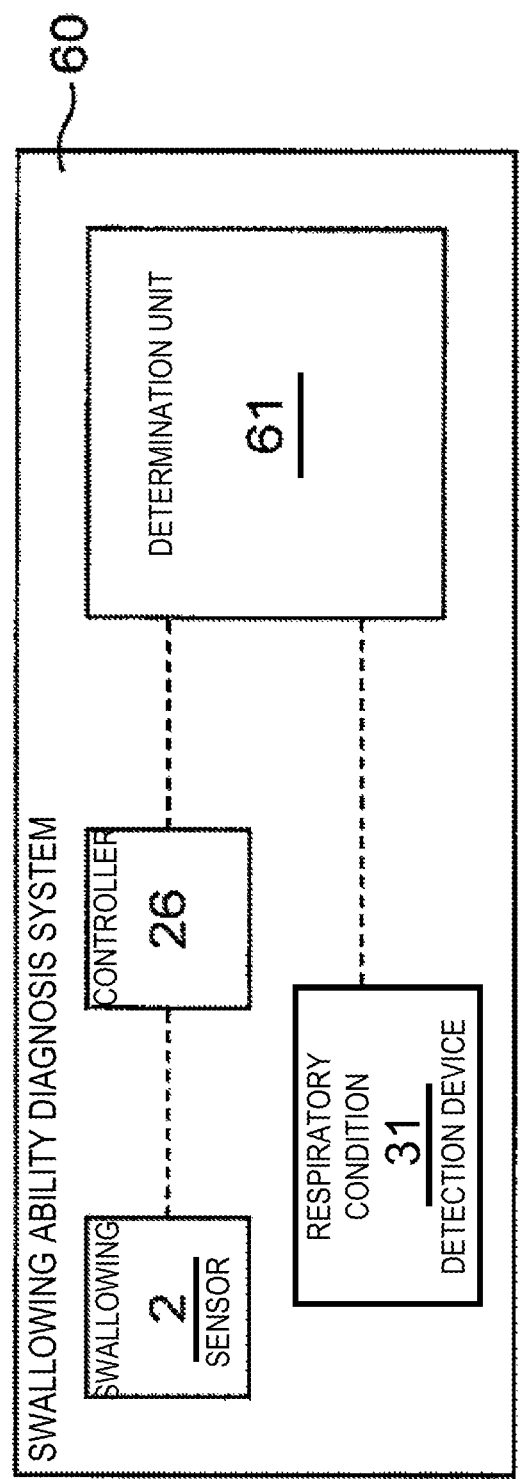
FIG. 13 is a block diagram representing the schematic configuration of a swallowing ability diagnosis system according to a modification.

Next, FIG. 13 illustrates a modification of the swallowing ability diagnosis system 50 illustrated in FIG. 12. A swallowing ability diagnosis system 60 illustrated in FIG. 13 further includes, in addition to the above-described swallowing sensor 2 and controller 26, a respiratory condition (or state) detection device (sensor) 31. The respiratory condition detection device 31 is a device that detects the respiratory condition or state of the person 4, and includes, for example, a pressure sensor. When the respiratory condition detection device 31 includes a pressure sensor, the respiratory condition detection device 31 is connected to a tube inserted through the nose of the person 4 and detects the respiratory condition on the basis of the exhalation pressure of the person 4. The respiratory condition detection device 31 is electrically coupled to a determination unit 61 along with the controller 26. The swallowing sensor 2 and the controller 26 are connected to the determination unit 61 in parallel with the respiratory condition detection device 31. The determination unit 61 determines (diagnoses) the swallowing ability of the person 4 by processing a detection result obtained by the swallowing sensor 2, which is from the controller 26, and a detection result obtained by the respiratory condition detection device 31. According to such a configuration, because the swallowing ability of the person 4 is comprehensively determined by taking into consideration the respiratory state of the person 4 in addition to the result based on the swallowing sensor 2, the swallowing ability of the person 4 can be more accurately diagnosed.

Although the present disclosure has been described with reference to the above-described embodiment, the present disclosure is not limited to the above-described embodiment. For example, although the case in which the adhesive layer 10 has a shape that covers the entirety of the main side 8a, which is one of two main sides of the detector 8, has been described in the embodiment, the embodiment is not limited to this case, and the adhesive layer 10 may partially cover the main side 8a, which is one of two main sides of the detector 8.

In addition, although the case in which the adhesive layer 10 includes the base material 10a has been described in the embodiment, the embodiment is not limited to this case, and the adhesive layer 10 may include only the layer 10b containing an adhesive component, without necessarily including the base material 10a.

By appropriately combining arbitrary embodiments among the above-described various embodiments, advantageous effects of each of the embodiments may be achieved.

Although the present disclosure has been fully described in connection with embodiments with reference to the accompanying drawings, it is clear that various modifications and corrections will be apparent to those skilled in the art. Such modifications and corrections should be understood to be included in the scope of the present disclosure without departing from the scope of the present disclosure in accordance with the appended claims.

The disclosure of the specification, drawings, and claims of Japanese patent application No. 2016-097304 filed on May 13, 2016 and Japanese patent application No. 2016-097307 filed on May 13, 2016 is incorporated herein by reference in its entirety.

The invention claimed is:

1. A swallowing sensor configured to attach to a pharyngeal region of a subject and to measure a swallowing ability of the subject, comprising:
- a film-shaped detector configured to detect vibration based on displacement of and sound from the pharyngeal region;
- an adhesive layer that is provided on a first main side of the detector configured to adhere the detector to the pharyngeal region; and
- a sensing film that completely covers a second main side of the detector, the second main side being opposite the first main side,
- wherein the sensing film comprises an adhesive on a main side of the sensing film that covers the detector configured to adhere the main side of the sensing film to the second main side of the detector and to the pharyngeal region, and
- wherein the sensing film is configured to convey vibration to the detector.

2. The swallowing sensor according to claim 1, wherein an adhesive force of the adhesive layer is greater than an adhesive force of the sensing film.

3. The swallowing sensor according to claim 1, wherein a Young's modulus of the adhesive layer is less than a Young's modulus of the sensing film.

4. The swallowing sensor according to claim 1, wherein the sensing film comprises a supporting base layer having the adhesive on one side.

5. The swallowing sensor according to claim 1, wherein a thickness of the sensing film is 90 µm or greater.

6. The swallowing sensor according to claim 1, wherein the sensing film is a polyethylene or polyester.

7. The swallowing sensor according to claim 1, wherein the detector is a piezoelectric element or strain gauge configured to generate an electric charge signal based on a displacement of the detector.

8. The swallowing sensor according to claim 7, further comprising an amplifier circuit configured to amplify the electric charge signal generated by the detector.

9. The swallowing sensor according to claim 1, wherein the adhesive layer is a double-sided adhesive.

10. A swallowing ability diagnosis system comprising:
- the swallowing sensor according to claim 1; and
- at least one controller or microcomputer configured to process a detection result of the swallowing sensor, and to determine the swallowing ability of the subject based on the processed detection result.

11. The swallowing ability diagnosis system according to claim 10, further comprising:
- a respiratory condition or state sensor configured to detect a respiratory condition or state of the subject,
- wherein the at least one controller or microcomputer is further configured to determine the swallowing ability of the subject based on the processed detection result and the detected respiratory condition.

* * * * *